United States Patent
Brittain et al.

(10) Patent No.: US 10,376,464 B2
(45) Date of Patent: *Aug. 13, 2019

(54) CHARACTERIZATION OF THE COCRYSTAL PRODUCTS FORMED BY METOPROLOL AND DABIGATRAN BASES WITH L-THEANINE

(71) Applicant: THEAPRIN PHARMACEUTICALS INC., Hauppauge, NY (US)

(72) Inventors: Harry G. Brittain, Milford, NJ (US); Philip V. Felice, Smithtown, NY (US)

(73) Assignee: THEAPRIN PHARMACEUTICALS INC., Hauppauge, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/284,074

(22) Filed: Oct. 3, 2016

(65) Prior Publication Data
US 2017/0143838 A1   May 25, 2017

Related U.S. Application Data

(60) Provisional application No. 62/260,043, filed on Nov. 25, 2015.

(51) Int. Cl.
| | | |
|---|---|---|
| *C07C 409/44* | (2006.01) | |
| *A61K 9/00* | (2006.01) | |
| *C07D 401/12* | (2006.01) | |
| *A61K 31/138* | (2006.01) | |
| *A61K 31/198* | (2006.01) | |
| *A61K 31/4439* | (2006.01) | |
| *A61K 9/14* | (2006.01) | |
| *C07C 217/32* | (2006.01) | |
| *C07C 229/24* | (2006.01) | |
| *C07C 237/06* | (2006.01) | |

(52) U.S. Cl.
CPC .......... *A61K 9/0056* (2013.01); *A61K 9/0019* (2013.01); *A61K 9/0053* (2013.01); *A61K 9/145* (2013.01); *A61K 31/138* (2013.01); *A61K 31/198* (2013.01); *A61K 31/4439* (2013.01); *C07C 217/32* (2013.01); *C07C 229/24* (2013.01); *C07C 237/06* (2013.01); *C07D 401/12* (2013.01)

(58) Field of Classification Search
CPC ..... C07C 237/08; C07C 217/54; A61K 9/145; A61K 9/0053; A61K 9/0019; A61K 9/0056; A61K 31/198; A61K 31/138; A61K 31/4439; C07D 401/12
USPC .......................................................... 562/1
See application file for complete search history.

(56) References Cited

U.S. PATENT DOCUMENTS

2010/0286099 A1* 11/2010 Brittain ................ A61K 31/198
                                                             514/162

OTHER PUBLICATIONS

Citizendium, Metoprolol, the Citizens' compendium, Dec. 2009, p. 1-3. (Year: 2009).*

Kimura, K. et al., "L-Theanine reduces psychological and physiological stress responses", Biol Psychol., Jan. 2007; 74 (1); 39-45; Epub Aug. 22, 2006; http://www.ncbi.nlm.nih.gov/pubmed/16930802.

(Continued)

*Primary Examiner* — Taylor V Oh
(74) *Attorney, Agent, or Firm* — Morgan, Lewis & Bockius LLP

(57) ABSTRACT

Cocrystal compositions of metoprolol and dabigatran bases with enantiomers of theanine.

12 Claims, 4 Drawing Sheets

(56) References Cited

OTHER PUBLICATIONS

Sadzuka, Yasuyuki, et al., "Enhancement of the activity of doxorubicin by inhibition of glutamate transporter", Toxicology Letters 123 (2001) 159-167, Elsevier Science Ireland Ltd.
Pradaxa Package Insert, Boehringer Ingelheim Pharmaceuticals, Inc., Sep. 2014.
http://www.l-glutaminebenefits.com/l-glutamine-side-effects/, "L-Glutamine Benefits—The Benefits of of l-glutamine, L-Glutamine Side Effects", Aug. 2, 2013.
http://www.mayoclinic.org/drugs-supplements/glutamine-oral-route/side-effects/DRG-20064099, Glutamine (Oral Route) Side Effects.
https://en.wikipedia.org/wiki/Long_QT_syndrome, "Long QT syndrome".

\* cited by examiner

Wavenumber (cm⁻¹)

CHARACTERIZATION OF THE COCRYSTAL PRODUCTS FORMED BY METOPROLOL AND DABIGATRAN BASES WITH L-THEANINE

FIELD AND BACKGROUND OF THE INVENTION

Field of the Invention

The present invention relates to preparation and characterization of the co-crystal products formed by metoprolol and dabigatran bases with L-theanine.

Background of the Invention

The ongoing interest in modification of drug substances whose physical properties are less than desirable has led to significant study of issues associated with polymorphism and solvatomorphism. More recently, it has been recognized that many substances may cocrystallize in a single continuous lattice structure, leading pharmaceutical scientists into new areas of crystal engineering. Cocrystals are mixed crystals where the cocrystal is a structurally homogeneous crystalline material that has been formed from discrete neutral molecular species that are solids at ambient temperatures.

Cocrystals represent novel forms of drug substances that would be suitable for incorporation in pharmaceutical solid dosage forms, and should enable formulation scientists to overcome a variety of problems that are encountered during development of traditional formulations. One could consider cocrystals as being an alternative to polymorphs, solvatomorphs, and salts, as cocrystals represent a different approach to solve problems related to dissolution, crystallinity, hygroscopicity, etc.

Unfortunately, it is not yet possible to predict whether two substances will cocrystallize or not, and therefore cocrystal screening studies are largely empirical in nature.

Thrombin is a serine protease which enables the conversion of fibrinogen into fibrin during the coagulation cascade resulting in clot formation. Dabigatran, being a direct inhibitor of thrombin, blocks clot formation.

Epinephrine (Adrenalin) an arrhythmogenic catecholamine, is a powerful cardiac stimulant acting directly on the B1 receptors of the myocardium, nodal tissue, and conducting system of the heart resulting in an increased heart rate.

Metoprolol (Lopressor) whose mechanism of action as a selective B1 receptor antagonist (class II antiarrhythmic beta adrenergic blocker) acts directly on the B1 receptors of the myocardium, nodal tissue, and conducting system of the heart antagonizing the cardiac action of catecholamine like epinephrine, thereby slowing the heart rate. Metoprolol prevents epinephrine from binding to the B1 receptors by competing for the binding site.

Metoprolol is an FDA approved medication indicated in the treatment of the following arrhythmias in stable patients: ventricular tachycardia, atrial fibrillation with rapid ventricular response, atrial flutter, paroxysmal supraventricular tachycardia (except in patients with Wolff-Parkinson-White Syndrome), multifocal atrial tachycardia (except in patients with COPD).

The underlying cause of any arrhythmia needs to be determined and treated. Some causes of arrhythmias that need to be ruled out include: hypomagnesemia, hypokalemia, hyperthyroidism, digoxin toxicity, theophylline toxicity, illicit drug use (e.g., cocaine, phencyclidine, MDMA (3,4-methylenedioxymethamphetamine) "molly" or "ecstasy"); aerosol propellant inhalation, glue inhalation, lithium toxicity, tricyclic antidepressant toxicity, monoamine oxidase inhibitor toxicity, serotonin syndrome, drug-induced (pentamidine, albuterol, and vasopressors like dopamine, epinephrine, norepinephrine), pulmonary embolism, myocardial infarction, cardiomyopathy, hypoxia, licorice root tea (glycyrrhizin glabra root) when consumed regularly and in excessive amounts, and genetic etiologies. The aforementioned list of etiologies of arrhythmias is non-limiting.

Metoprolol is used in the prevention of stress-induced arrhythmias associated with inherited long QT syndrome 1 and long QT syndrome 2 (See "Long QT Syndrome." N.p., n.d. Web. wikipedia.org/wiki/Long_QT_syndrome).

Theanine which is 5-N-Ethyl glutamine, is an ethylamide of glutamine acid. In the medical literature, theanine is known to slow the heart rate due to an attenuation of sympathetic nervous system activation (See Kimura, K. "L-Theanine Reduces Psychological and Physiological Stress Responses." N.p., n.d. Web. ncbi.nim.nih.gov/pubmed/16930802).

Glutamine is known to increase the heart rate (See "Glutamine (Oral Route) Side Effects." N.p., n.d. Web. mayoclinic.org/drugs-supplements/glutamine-oral-route/side-effects/DRG-20064099. Drug information provided by Micromedex; "L-Glutamine Benefits." N.p., n.d. Web. l-glutaminebenefits.com/l-glutamine-side-effects).

Cancer cells use glutathione to detoxify doxorubicin and escort the drug out of cells. Theanine is able to interfere with this process due to its structural similarity to glutamate (steric hindrance) (See Table I). Sadzuka found that theanine could block the export of doxorubicin (Adriamycin) from cancer cells by blocking the glutamate and glutathione transporter mechanisms, resulting in an elevated level of doxorubicin within cancer cells which strongly inhibits the tumor (See Sadzuka, Yasuyuki, Tomomi Sugiyama, Toshihiro Suzuki, and Takashi Sonobe. "*Enhancement of the Activity of Doxorubicin by Inhibition of Glutamate Transporter.*" Toxicology Letters 123.2-3 (2001): 159-67).

Coformers depicted below are highly structurally related to L-theanine:

TABLE I

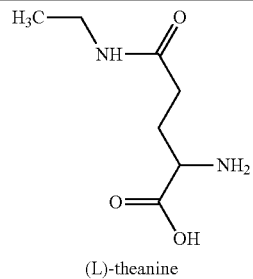

(L)-theanine

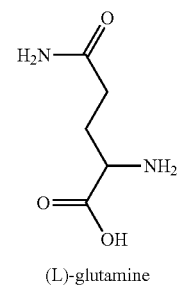

(L)-glutamine

TABLE I-continued

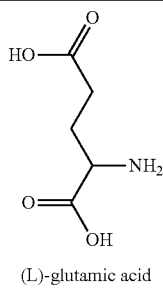

(L)-glutamic acid

Given the structural similarity of glutamine with theanine, and the fact that glutamine increases the heart rate might have led one to deduce that theanine would also increase the heart rate. In spite of this expectation, theanine does in fact slow the heart rate. Therefore, since one could not have predicted that theanine would slow the heart rate, the effects of the metoprolol-theanine cocrystal represent an unexpected result.

The various features of novelty which characterize the invention are pointed out with particularity in the claims annexed to and forming a part of this disclosure. For a better understanding of the invention, its operation advantages and specific objects attained by its uses, reference is made to the accompanying figures and descriptive matter in which a preferred embodiment of the invention is illustrated.

SUMMARY OF THE INVENTION

It is therefore an object of the present invention to provide a method utilizing crystallization of metoprolol and dabigatran bases with L-Theanine which is readily administrable to individuals through a variety of media.

It is also an object of the present invention to provide a cocrystal composition composed of a quantity of a theanine enantiomer, and a quantity of a drug from a class selected from the group consisting of beta blockers and direct thrombin inhibitors.

It is a further object to provide a cocrystal composition which includes a quantity of a theanine enantiomer, and a quantity of a drug selected from the group which includes a metoprolol base and a dabigatran base.

It is also an object to provide a cocrystal composition which includes a quantity of a theanine enantiomer, and a quantity of a drug for treating arrhythmias in stable patients, including ventricular tachycardia, atrial fibrillation with rapid ventricular response, atrial flutter, paroxysmal supraventricular tachycardia (except in patients with Wolff-Parkinson White Syndrome), and multifocal atrial tachycardia (except in patients with COPD). The present invention satisfies these and others medical needs and overcomes deficiencies found in the prior art.

It is also an object to provide a cocrystal composition which includes a quantity of a theanine enantiomer, and a quantity of a drug for reduction of risk of stroke and systemic embolism in non-valvular atrial fibrillation, treatment of deep vein thrombosis and pulmonary embolism in patients who have been treated with a parenteral anticoagulant (including patients who have been treated with a parenteral anticoagulant for 5-10 days), and reduction in the risk of recurrence of deep vein thrombosis and pulmonary embolism (See *Medication Guide (Package Insert) Pradaxa (Dabigatran Etexilate Mesylate) Indications and Usage*, Distributed by Boehringer Ingelheim Pharmaceuticals Inc.; Ridgefield, Conn., Revised September 2014). The present invention satisfies these and others medical needs and overcomes deficiencies found in the prior art.

In certain embodiments, the theanine enantiomer is selected from the group which includes L-theanine, D-theanine, and DL-theanine.

In yet further embodiments, the theanine enantiomer is selected from the group which includes an alpha variant of theanine and a beta variant of theanine.

In certain of these embodiments, the alpha variant of theanine is selected from the group which includes L-Northeanine, D-Northeanine, DL-Northeanine, L-homotheanine, D-homotheanine, DL-homotheanine, L-bishomotheanine, D-bishomotheanine, and DL-bishomotheanine.

In certain other of these embodiments the alpha variant of theanine is a homologous analog of theanine.

In certain other of these embodiments, the alpha variant of theanine contains a functional group selected from the group which includes linear, cyclic, or branched alkyl and derivatives thereof, linear, cyclic, or branched alkenyl and derivatives thereof, and aromatic radicals and derivatives thereof.

In some of these embodiments, the aromatic radicals are aryl radicals.

In further embodiments, the theanine enantiomer is a racemic mixture of a beta variant of theanine containing a functional group selected from the group which includes linear, cyclic, or branched alkyl groups and derivatives thereof, linear, cyclic, or branched alkenyl groups and derivatives thereof, and aromatic radicals and derivatives thereof.

In certain other of these embodiments, the aromatic radicals are aryl radicals.

In certain embodiments the theanine enantiomer is an S enantiomer of a beta variant of theanine containing a functional group selected from the group which includes linear, cyclic, or branched alkyl groups and derivatives thereof, linear, cyclic, or branched alkenyl groups and derivatives thereof, and aromatic radicals and derivatives thereof.

In further embodiments, the aromatic radicals are aryl radicals.

In yet further embodiments, the theanine enantiomer is an R enantiomer of a beta variant of theanine containing a functional group selected from the group which includes linear, cyclic, or branched alkyl groups and derivatives thereof, linear, cyclic, or branched alkenyl groups and derivatives thereof, and aromatic radicals and derivatives thereof.

In certain of these embodiments, the aromatic radicals are aryl radicals.

In certain of these embodiments, the mixture further includes a sugar alcohol.

In certain of these embodiments, the sugar alcohol has a configuration selected from the group which includes the L-configuration and the D-configuration.

It is also an object to provide a cocrystal composition which includes a quantity of L-theanine, and a quantity of a chemical composition selected from the group which includes metoprolol base and dabigatran base.

Embodiments of the present invention are directed to a cocrystal composition including a quantity of a theanine enantiomer and drugs from the following drug classes: beta blockers and direct thrombin inhibitors.

In addition, embodiments of the present invention are directed to compositions including a quantity of a theanine enantiomer and the following drugs: metoprolol base and dabigatran base.

Embodiments of the present invention are also directed to compositions including a quantity of a theanine enantiomer and drugs for treating the following conditions: Arrhythmias in stable patients: ventricular tachycardia, atrial fibrillation with rapid ventricular response, atrial flutter, paroxysmal supra-ventricular tachycardia (except in patients with Wolff Parkinson-White Syndrome), multifocal atrial tachycardia (except in patients with COPD); reduction of risk of stroke and systemic embolism in nonvalvular atrial fibrillation, treatment of deep vein thrombosis and pulmonary embolism in patients who have been treated with a parenteral anticoagulant (including patients who have been treated with a parenteral anticoagulant for 5-10 days), and reduction in the risk of recurrence of deep vein thrombosis and pulmonary embolism.

These and other non-limiting aspects and/or objects of the disclosure are more particularly described below. The various features of novelty which characterize the invention are pointed out with particularity in the claims annexed hereto and forming a part of the disclosure. For a better understanding of the invention, its operating advantages and specific benefits attained by its uses, reference is made to the accompanying drawings and descriptive matter in which exemplary embodiments of the invention are illustrated.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION OF THE PREFERRED EMBODIMENTS

Figure 1:
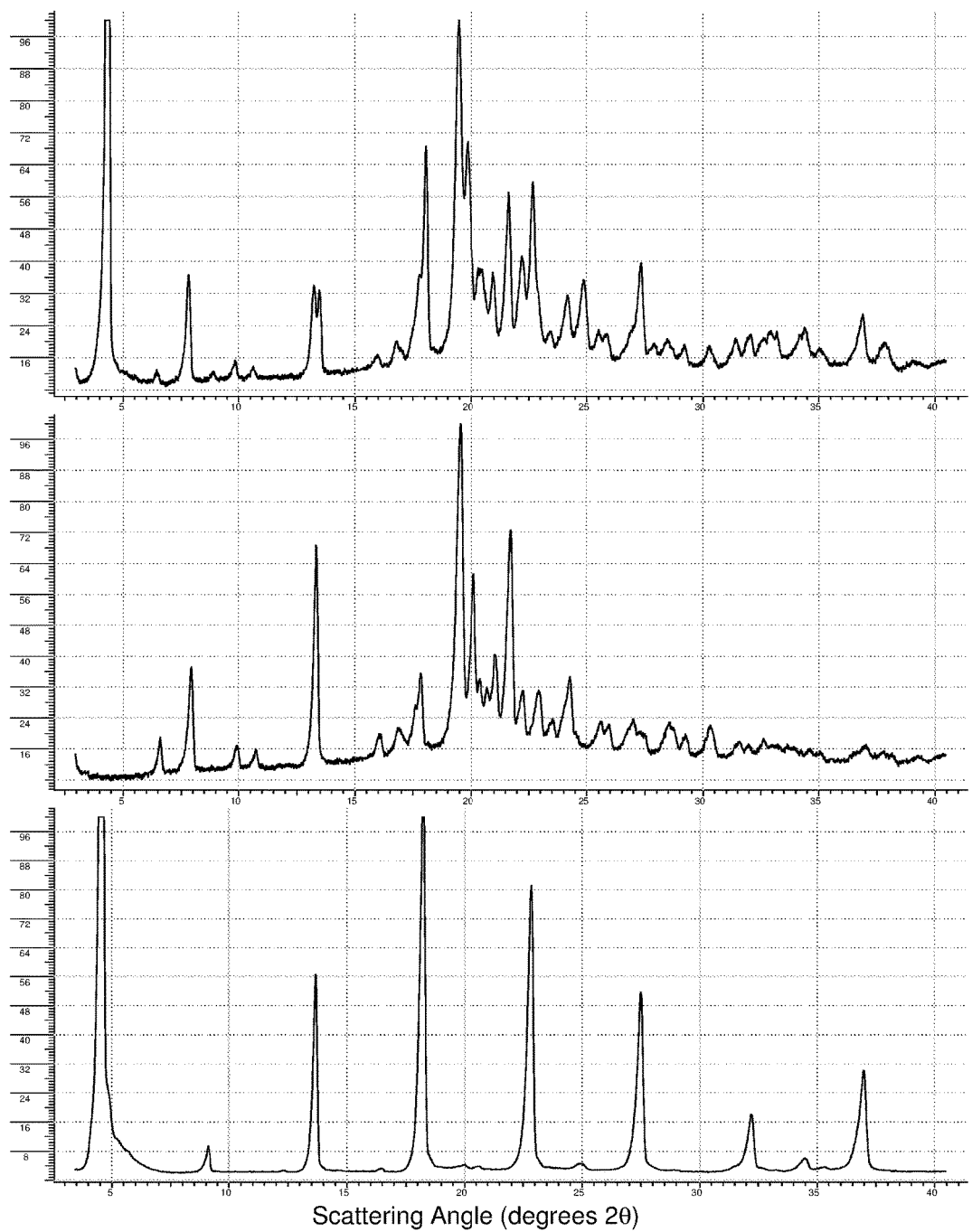
FIG. 1 depicts XRPD patterns of L-theanine (lower trace), metoprolol (middle trace), and the L-theanine/metoprolol cocrystal product (upper trace)

Embodiments of the present invention employ theanine (5-N-ethyl glutamine), a non-protein amino acid found naturally in green tea leaves.

Embodiments of the present invention include cocrystallization of metoprolol base with theanine (5-N-ethyl-glutamine).

Embodiments of the present invention also include cocrystallization of dabigatran base with theanine (5-N-ethyl-glutamine).

Embodiments of the present invention further include cocrystal compositions of the following medication groups with theanine (5-N-ethyl-glutamine): beta blockers, direct thrombin inhibitors.

The present invention is directed to, among other things, cocrystal compositions of the following drug classes with theanine (5-N-ethyl-glutamine): beta blockers, direct thrombin inhibitors.

Further, the theanine contained in compositions according to embodiments of the present invention may be of any of L-form, D-form, DL-form.

According to embodiments of the present invention the L-, D-, DL-alpha amino acids of Theanine and their side-chain carbon homologues (nor, homo, and bishomologues) may have a functional R-group, where R1 may contain linear, cyclic, or branched alkyl groups and derivatives thereof; linear, cyclic, or branched alkenyl groups and derivatives thereof; and aromatic radicals and derivatives thereof. In embodiments of the present invention, the aromatic radicals may be aryl radicals.

According to the embodiments of the present invention in addition to L-theanine, other analogues include D-Theanine, racemic theanine or D, L-theanine and its congeners including beta and reverse beta amino acid forms, shortened or nor-theanine (aspartic acid analogue), and the lengthened homo-theanines and their isomers. Further, gamma alkylamido analogues extend a full range of molecular property for drug cocrystals.

According to the embodiments of the present invention the single enantiomers (S and R) and racemic forms (S, R-mixture) of the beta amino acids of theanine may have a functional R-group, where R1 may contain linear, cyclic, or branched alkyl groups and derivatives thereof; linear, cyclic, or branched alkenyl groups and derivatives thereof; and aromatic radicals and derivatives thereof. In embodiments of the present invention, the aromatic radicals may be aryl radicals.

Embodiments of the present invention may include cocrystal compositions of drugs from the classes listed below and the enantiomers, L- and D-isomers, D, L-racemic mixture, S- and R-isomers, S, R-racemic mixtures, all rotamers, tautomers, salt forms, and hydrates of the alpha and beta amino acids of theanine in which the N-substituted functional R1-group [C4 or gamma-CH2-C(O)—NR1] may contain linear, cyclic, or branched alkyl groups and derivatives thereof; linear, cyclic or branched alkenyl groups and derivatives thereof; and aromatic radicals (which may be aryl radicals) and derivatives thereof making up all the analogue forms of theanine: beta blockers, direct thrombin inhibitors.

Derivatives prepared using metoprolol base/L-theanine cocrystal compositions according to embodiments of the present invention can be administered via intravenous, sublingual (including as an orally disintegrating tablet), and orally (including as a tablet).

Derivatives prepared using dabigatran base/L-theanine cocrystal compositions according to embodiments of the present invention can be administered via sublingual, and orally.

The pharmaceutical compositions according to embodiments of the present invention may be prepared as oral solids (tablets, oral disintegrating tablets, effervescent tablets, capsules), oral liquids, hard or soft gelatin capsules, quick dissolves, controlled release, modified release, extended release, slow release, sustained release, syrups, suspensions, granules, wafer (films), pellets, lozenges, powders, parenteral/injectable powders or granules that are pre-mixed or reconstituted.

Cocrystals according to embodiments of the present invention may be used to improve one or more physical properties such as solubility, stability, and dissolution rate of the active pharmaceutical ingredient of a selected treatment or prevention.

Next, the present invention will be described in further detail by means of examples, without intending to limit the scope of the present invention to these examples alone. The following are exemplary formulations with cocrystal compositions of the following medication groups with L-theanine in accordance with the present invention: beta blockers, direct thrombin inhibitors.

EXPERIMENTAL DETAILS, PREPARATION OF THE COCRYSTAL PRODUCTS

Example 1

Preparation of the L-theanine/metoprolol cocrystal product was performed as follows: 0.329 g of metoprolol (1.231 mmol) and 0.214 g of L-theanine (1.228 mmol) were weighed directly into the bowl of an agate mortar, and wetted with 70% isopropanol to form a moderately thick slurry. The slurry was thoroughly ground at the time of mixing, and then periodically re-ground until the contents were dry.

Example 2

Preparation of the L-theanine/dabigatran cocrystal product was performed as follows: 0.296 g of dabigatran (0.628 mmol) and 0.111 g of L-theanine (0.637 mmol) were weighed directly into the bowl of an agate mortar, and wetted with 70% isopropanol to form a moderately thick slurry. The slurry was thoroughly ground at the time of mixing, and then periodically re-ground until the contents were dry.

Instrumental Descriptions and Methodology

X-ray powder diffraction (XRPD) patterns were obtained using a Rigaku MiniFlex powder diffraction system, equipped with a horizontal goniometer operating in the θ/2θ mode. The X-ray source was nickel-filtered Kα emission of copper (1.54184 Å). The sample was packed into the sample holder using a back-fill procedure, and were scanned over the range of 3.25 to 40 degrees 2θ at a scan rate of 0.5 degrees 2θ/min. Using a data acquisition rate of 1 point per second, the scanning parameters equate to a step size of 0.0084 degrees 2θ. Calibration of the diffractometer system was effected using purified talc as a reference material.

Fourier-transform infrared absorption (FTIR) spectra were obtained at a resolution of 4 cm$^{-1}$ using a Shimadzu model 8400S spectrometer, with each spectrum being obtained as the average of 40 individual spectra. The data were acquired using the attenuated total reflectance (ATR) sampling mode, where the samples were clamped against the ZnSe crystal of a PIKE MIRacle™ single reflection horizontal ATR sampling accessory. The intensity scale for all spectra was normalized so that the relative intensity of the most intense peak in the spectrum 100%.

Measurements of differential scanning calorimetry (DSC) were obtained on a TA Instruments 2910 thermal analysis system. Samples of approximately 1-2 mg were accurately weighed into an aluminum DSC pan, and then covered with an aluminum lid that was inverted and pressed down so as to tightly contain the powder between the top and bottom aluminum faces of the lid and pan. All samples were heated at a rate of 10° C./min, with the dabigatran-related samples being heated over the temperature range of 25-300° C., while the metoprolol-related samples were heated over the temperature range of 25-125° C.

Results

The Theanine/Metoprolol System

The XRPD patterns of L-theanine, metoprolol, and the L-theanine/metoprolol cocrystal product are shown in FIG. 1. Comparison of the diffraction patterns reveals that the XRPD pattern of the cocrystal product contains scattering peaks at angles of 19.85 and 24.85 degrees 2θ that were not present in the XRPD patterns of the reactants. In addition, many of the peaks in the XRPD pattern of the cocrystal were found to be shifted to lower angles relative to their corresponding peaks in the XRPD patterns of the reactants. Since the XRPD pattern of the cocrystal product is different from the superimposed XRPD patterns of the reactants, this demonstrates that an authentic cocrystal is formed by L-theanine with metoprolol.

Figure 2:
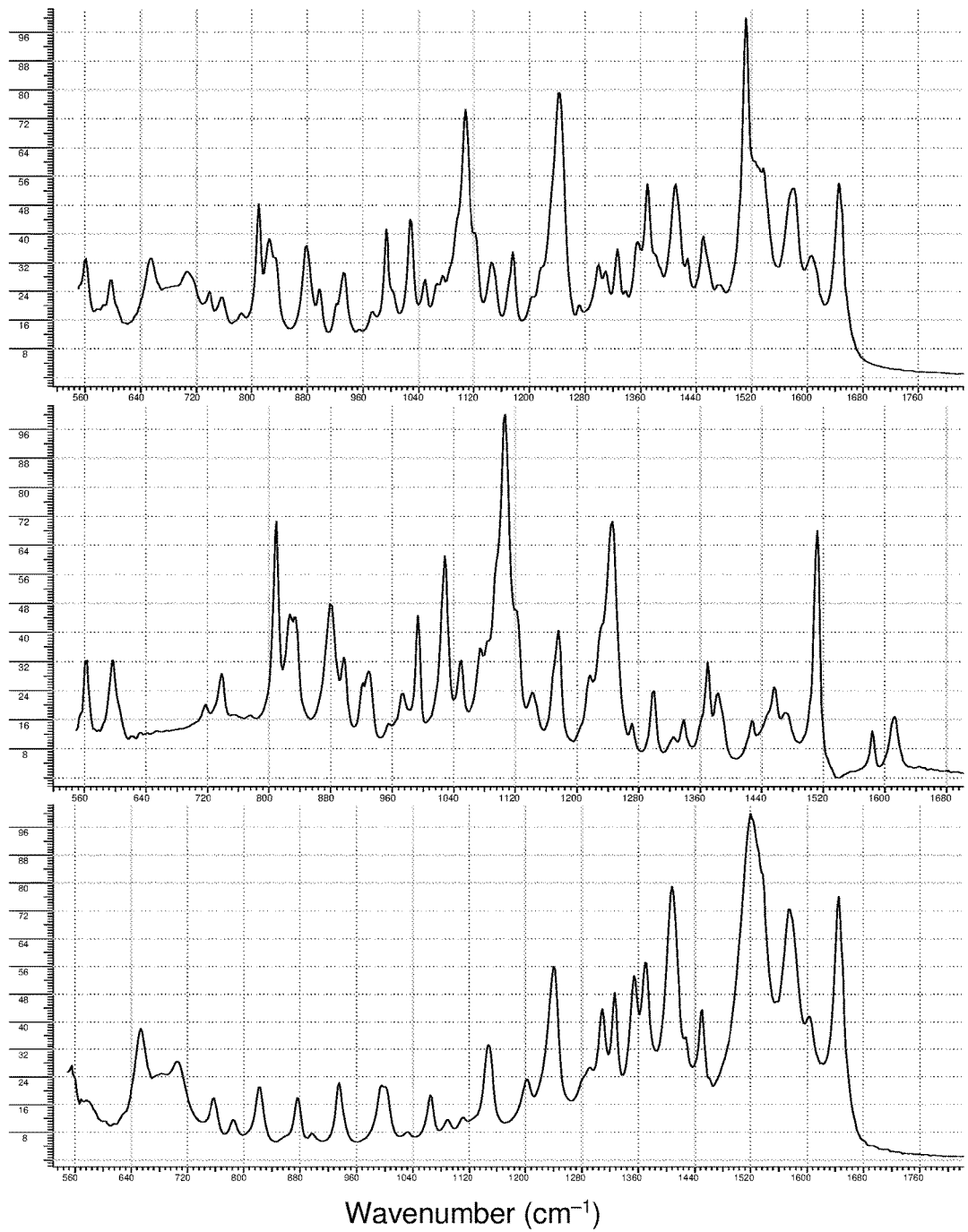
FIG. 2 depicts fingerprint region FTIR spectra of L-theanine (lower trace), metoprolol (middle trace), and the L-theanine/metoprolol cocrystal product (upper trace)

The FTIR spectra in the fingerprint region (which is the most diagnostic region for critical study) of L-theanine, metoprolol, and the L-theanine/metoprolol cocrystal product are shown in FIG. 2. The most significant difference in the FTIR spectra is noted in the region around 1520 cm$^{-1}$, where the FTIR bands of the cocrystal product are substantially altered relative to the bands of the reactants in this same region, providing evidence for perturbation in the patterns of these vibrational motions. In addition, a number of other vibrational bands in the spectrum of the cocrystal product are shifted by several wavenumbers relative to the corresponding bands of the reactants.

Finally, the DSC melting endotherm of the L-theanine/metoprolol cocrystal product was found to exhibit a peak at a temperature of 42° C., which is significantly lower than the peak observed for metoprolol itself (temperature of 53.5° C.).

The Theanine/Dabigatran System

Figure 3:
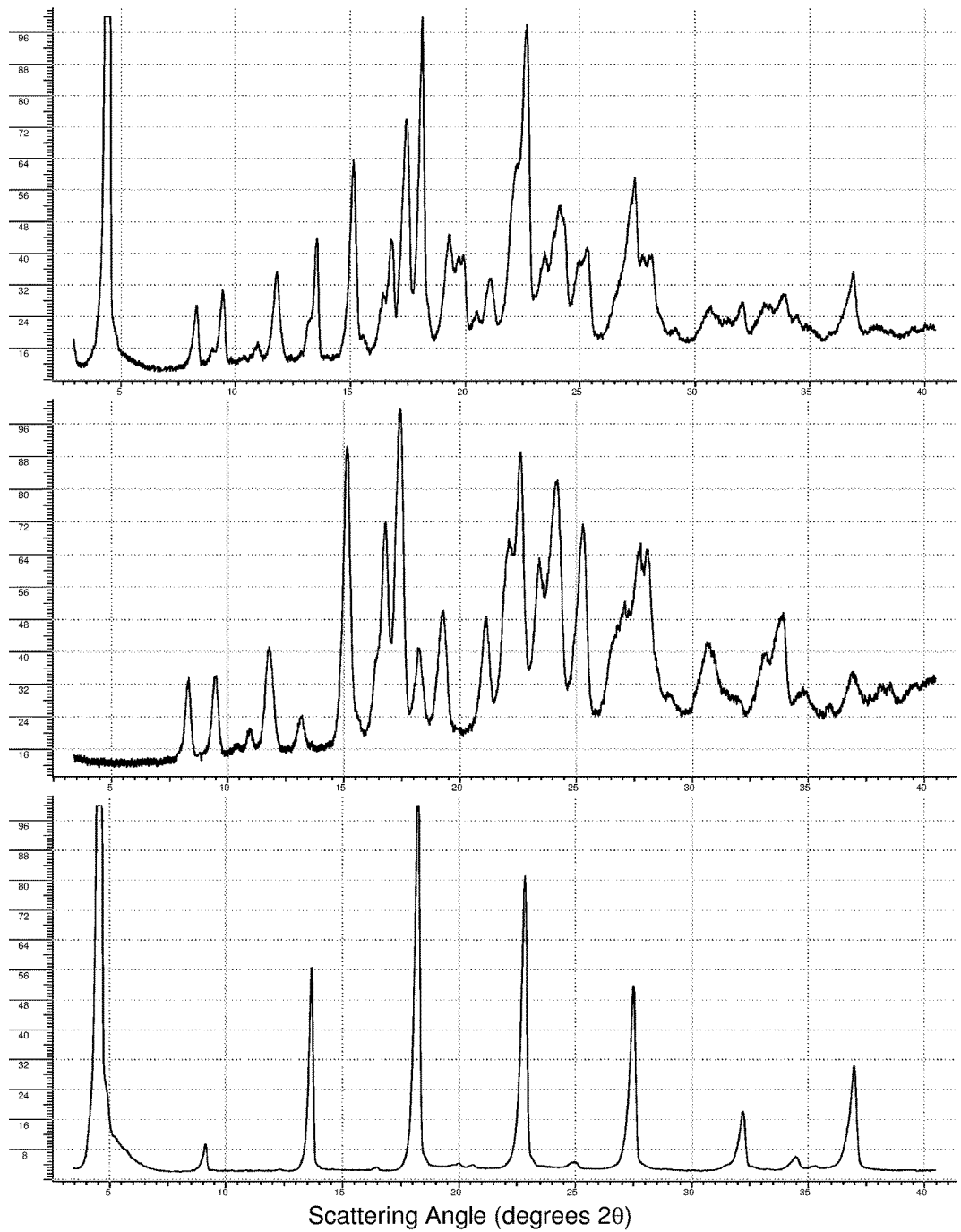
FIG. 3 depicts XRPD patterns of L-theanine (lower trace), dabigatran (middle trace), and the L-theanine/dabigatran cocrystal product (upper trace)

The XRPD patterns of L-theanine, dabigatran, and the L-theanine/dabigatran cocrystal product are shown in FIG. 3. Comparison of the diffraction patterns reveals that the XRPD pattern of the cocrystal product contains scattering peaks the region of 19.5 to 21 degrees 2θ that were not present in the XRPD patterns of the reactants. In addition, several of the peaks in the XRPD pattern of the cocrystal were found to be shifted angles relative to their corresponding peaks in the XRPD patterns of the reactants. Since the XRPD pattern of the cocrystal product is different from the superimposed XRPD patterns of the reactants, this demonstrates that an authentic cocrystal is formed by L-theanine with dabigatran.

Figure 4:
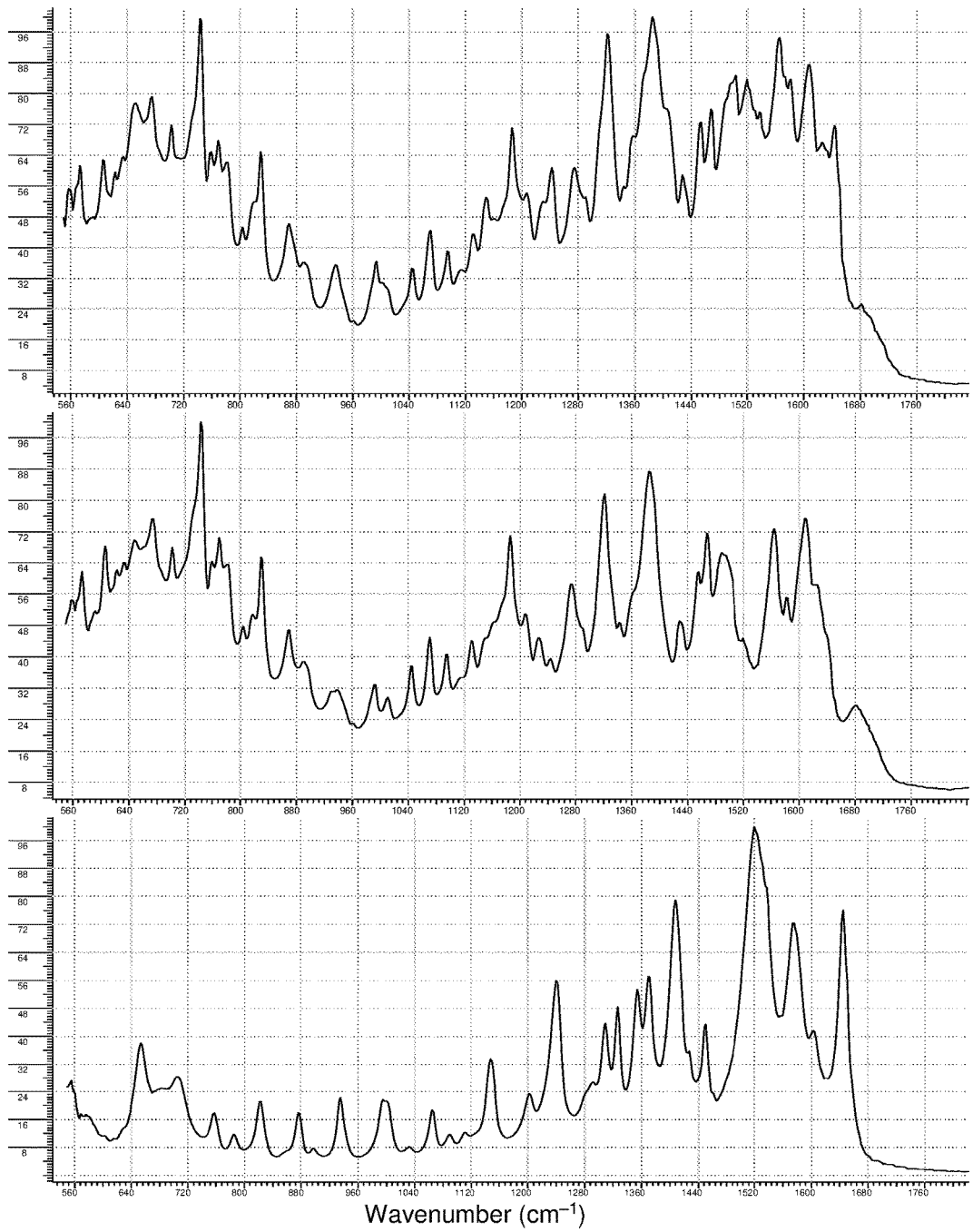
FIG. 4 depicts fingerprint region FTIR spectra of L-theanine (lower trace), dabigatran (middle trace), and the L-theanine/dabigatran cocrystal product (upper trace).

The FTIR spectra in the fingerprint region (which is the most diagnostic region for critical study) of L-theanine, dabigatran, and the L-theanine/dabigatran cocrystal product are shown in FIG. 4. The most significant difference in the FTIR spectra is noted especially in the region of 1475 to 1600 cm$^{-1}$, where the FTIR bands of the cocrystal product are substantially altered relative to the bands of the reactants in this same region.

In addition, a number of other vibrational bands in the spectrum of the co-crystal product are shifted by several wavenumbers relative to the corresponding bands of the reactants.

The DSC melting endotherm of the L-theanine/dabigatran cocrystal product was found to exhibit a peak at a temperature of 218° C., which is significantly lower than the peak observed for dabigatran itself (temperature of 281.5° C.).

Embodiments of the present invention include cocrystal compositions of L-Theanine combined with the drugs listed in the table below to treat the following conditions:

| Conditions | Drug |
|---|---|
| Arrhythmias in stable patients: ventricular tachycardia, atrial fibrillation with rapid ventricular response, atrial flutter, paroxysmal supra-ventricular tachycardia (except in patients with Wolff-Parkinson-White Syndrome), and multifocal atrial tachycardia (except in patients with COPD). | Metoprolol Base |
| Reduction of risk of stroke and systemic embolism in non-valvular atrial fibrillation, treatment of deep vein thrombosis and pulmonary embolism in patients who have been treated with a parenteral anticoagulant for days (patients who have been treated with a parenteral anticoagulant for 5-10 days), and reduction in the risk of recurrence of deep vein thrombosis and pulmonary embolism. | Dabigatran Base |

While a specific embodiment of the invention has been shown and described in detail to illustrate the application of the principles of the invention, it will be understood that the invention may be embodied otherwise without departing from such principles.

What is claimed is:

1. A water-soluble composition consisting essentially of: a cocrystal composition containing a quantity of a theanine enantiomer and a quantity of a drug from a class selected from the group consisting of adrenergic beta blockers and direct thrombin inhibitors.

2. The composition of claim 1, wherein the theanine enantiomer is selected from the group consisting of L-theanine, D-theanine and DL-theanine.

3. A cocrystal composition consisting essentially of: a quantity of a theanine enantiomer and a quantity of a metoprolol base.

4. A cocrystal composition comprising: a quantity of a theanine enantiomer and a quantity of dabigatran base.

5. The composition of claim 2, wherein the theanine enantiomer is selected from the group consisting of L-Northeanine, D-Northeanine, DL-Northeanine, L-homotheanine, D-homotheanine, DL-homotheanine, L-bishomotheanine, D-bishomotheanine, and DL-bishomotheanine.

6. The composition of claim 2, further comprising a sugar alcohol.

7. The composition of claim 6, wherein the sugar alcohol has a configuration selected from the group consisting of the L-configuration and the D-configuration.

8. A cocrystal composition consisting essentially of: a quantity of L-theanine; and a quantity of a chemical composition selected from the group consisting of metoprolol base and dabigatran base.

9. The water-soluble composition of claim 1, wherein the composition is formulated as an oral solid formulation, a tablet, an oral disintegrating tablet, an effervescent tablet, a capsule, an oral liquid, a hard gelatin capsule, a soft gelatin capsule, a quick dissolve formulation, a controlled release formulation, a modified release formulation, an extended release formulation, a slow release formulation, a sustained release formulation, a syrup, a suspension, a granule, a wafer, a films, a pellet, a lozenge, a powder, a parenteral powder, or an injectable powder.

10. The cocrystal composition of claim 3, wherein the composition is formulated as an oral solid formulation, a tablet, an oral disintegrating tablet, an effervescent tablet, a capsule, an oral liquid, a hard gelatin capsule, a soft gelatin capsule, a quick dissolve formulation, a controlled release formulation, a modified release formulation, an extended release formulation, a slow release formulation, a sustained release formulation, a syrup, a suspension, a granule, a wafer, a films, a pellet, a lozenge, a powder, a parenteral powder, or an injectable powder.

11. The cocrystal composition of claim 4, wherein the composition is formulated as an oral solid formulation, a tablet, an oral disintegrating tablet, an effervescent tablet, a capsule, an oral liquid, a hard gelatin capsule, a soft gelatin capsule, a quick dissolve formulation, a controlled release formulation, a modified release formulation, an extended release formulation, a slow release formulation, a sustained release formulation, a syrup, a suspension, a granule, a wafer, a films, a pellet, a lozenge, a powder, a parenteral powder, or an injectable powder.

12. The cocrystal composition of claim 8, wherein the composition is formulated as an oral solid formulation, a tablet, an oral disintegrating tablet, an effervescent tablet, a capsule, an oral liquid, a hard gelatin capsule, a soft gelatin capsule, a quick dissolve formulation, a controlled release formulation, a modified release formulation, an extended release formulation, a slow release formulation, a sustained release formulation, a syrup, a suspension, a granule, a wafer, a films, a pellet, a lozenge, a powder, a parenteral powder, or an injectable powder.

* * * * *